United States Patent [19]
Groger et al.

[11] Patent Number: 5,577,137
[45] Date of Patent: Nov. 19, 1996

[54] OPTICAL CHEMICAL SENSOR AND METHOD USING SAME EMPLOYING A MULTIPLICITY OF FLUOROPHORES CONTAINED IN THE FREE VOLUME OF A POLYMERIC OPTICAL WAVEGUIDE OR IN PORES OF A CERAMIC WAVEGUIDE

[75] Inventors: Howard P. Groger, Gainesville, Fla.; Peter Lo, Blacksburg, Va.; Russell J. Churchill, Radford, Va.; Martin Weiss, New Port Richey, Fla.; Shufang Luo, Blacksburg, Va.

[73] Assignee: American Research Corporation of Virginia, Radford, Va.

[21] Appl. No.: 392,152

[22] Filed: Feb. 22, 1995

[51] Int. Cl.$^6$ .......................... G02B 6/00; G01N 15/06
[52] U.S. Cl. .................... 385/12; 385/14; 385/37; 385/130; 385/131; 422/68.1; 250/227.11; 250/227.14; 250/576
[58] Field of Search ...................... 385/12, 14, 27, 385/30, 33, 37, 39, 129, 130, 131, 132, 141; 422/68.1, 73, 50, 57; 250/227.11, 227.14, 227.18, 227.23, 576

[56] References Cited

U.S. PATENT DOCUMENTS

| | | | |
|---|---|---|---|
| Re. 31,879 | 5/1985 | Lubbers et al. | 436/133 |
| 4,050,895 | 9/1977 | Hardy et al. | 385/12 X |
| 4,548,907 | 10/1985 | Seitz et al. | 436/163 |
| 4,582,809 | 4/1986 | Block et al. | 436/527 |
| 4,654,532 | 3/1987 | Hirschfeld | 250/458.1 |
| 4,803,049 | 2/1989 | Hirschfeld et al. | 422/58 |
| 4,815,843 | 3/1989 | Tiefenthaler et al. | 356/128 |
| 4,818,710 | 4/1989 | Sutherland et al. | 436/527 |
| 4,844,613 | 7/1989 | Batchelder et al. | 356/318 |
| 4,877,747 | 10/1989 | Stewart | 436/525 |

(List continued on next page.)

OTHER PUBLICATIONS

Levy, D., Journal Of Non–Crystalline Solids, vol. 147–148, pp. 508–517 (1992).

Reisfeld and Jorgensen, Structure And Bonding, pp. 208–256 (1992).

Zusman et al., Journal Of Non–Crystalline Solids, vol. 122, pp. 107–109 (1990).

(List continued on next page.)

*Primary Examiner*—Brian Healy
*Attorney, Agent, or Firm*—James Creighton Wray

[57] ABSTRACT

A fluorescent sensor for chemical analysis has a light source, an optical waveguide, and a detector. Fluorophores are associated with the optical waveguide. When an impervious waveguide is used, a fluorophore-containing layer is applied to a surface of the waveguide. The fluorophores are excited by a laser, a light emitting diode, an electroluminescent source or a lamp source emitting light propagating at angles to the waveguide. The light source is modulated. A mirror can be used to direct the light beam. The angle of light incidence on the waveguide can be altered by moving the waveguide itself. The waveguide traps the laser-induced fluorescence and projects fluorescence signals through a suitable filter to a photodetector or otherwise wavelength-specific photodetector positioned near the waveguide structure. Remote operation of the sensor is achieved using optical fibers. Patterned waveguides allow multiple excitation sources to illuminate multiple fluorescent probe materials. The change in fluorescence from each fluorophore is sensed as a vector response which is evaluated using digital signal processing. The sensor uses steady state fluorescence and fluorescence decay information to determine identity and concentration of analytes of interest. The invention is used for chemical analysis of gases or of liquid materials.

30 Claims, 2 Drawing Sheets

U.S. PATENT DOCUMENTS

| | | | |
|---|---|---|---|
| 4,880,752 | 11/1989 | Keck et al. | 435/7 |
| 4,889,690 | 12/1989 | Opitz et al. | 422/73 |
| 4,929,561 | 5/1990 | Hirschfeld | 436/116 |
| 4,980,278 | 12/1990 | Yamada et al. | 435/7 |
| 5,019,350 | 5/1991 | Rhum et al. | 422/82.07 |
| 5,045,282 | 9/1991 | Kritzman et al. | 422/56 |
| 5,093,266 | 3/1992 | Leader et al. | 436/68 |
| 5,094,517 | 3/1992 | Franke | 385/12 |
| 5,094,959 | 3/1992 | Allen et al. | 436/172 |
| 5,096,671 | 3/1992 | Kane et al. | 422/82.07 |
| 5,114,676 | 5/1992 | Leiner et al. | 422/82.06 |
| 5,120,131 | 6/1992 | Lukosz | 356/351 |
| 5,127,405 | 7/1992 | Alcala et al. | 128/633 |
| 5,154,890 | 10/1992 | Mauze et al. | 422/82.07 |
| 5,156,972 | 10/1992 | Issachar | 435/288 |
| 5,194,393 | 3/1993 | Hugl et al. | 436/525 |
| 5,196,709 | 3/1993 | Berndt et al. | 250/458.1 |
| 5,212,099 | 5/1993 | Marcus | 436/172 |
| 5,227,134 | 7/1993 | Janata | 422/82.08 |
| 5,237,631 | 8/1993 | Gavish et al. | 385/12 |
| 5,302,349 | 4/1994 | Dandliker et al. | 422/82.08 |
| 5,308,581 | 5/1994 | Lippitsch et al. | 422/82.08 |
| 5,315,672 | 5/1994 | Padovani | 385/12 |
| 5,324,635 | 6/1994 | Kawase et al. | 435/7.94 |
| 5,344,784 | 9/1994 | Attridge | 436/518 |
| 5,447,845 | 9/1995 | Chu et al. | 435/6 |

OTHER PUBLICATIONS

Janans et al., "Integrated Planar Optical Imaging System . . . ", Optics Letters, vol. 18, No. 19, pp. 1594–1596 (1993).

Tanguay, "Integrated Optical Information Processing", AFOSR–85–0312, AD–A201 016, Air Force Office Of Scientific Research (1988).

Feddersen et al., "Digital Parallel Acquisition . . . ", Review Of Scientific Instruments, vol. 60, No. 9, pp. 2929–2936 (1989).

Haruvy et al., "Sol–Gel Preparation of Optically–Clear Supported Thin Film Glasses . . . ", Supramolecular Architecture, pp. 405–424 (1992).

Haruvy et al., "Supported Sol–Gel Thin–Film Glasses . . . ", Submolecular Glass Chemistry & Physics, SPIE vol. 1590, pp. 59–70 (1991).

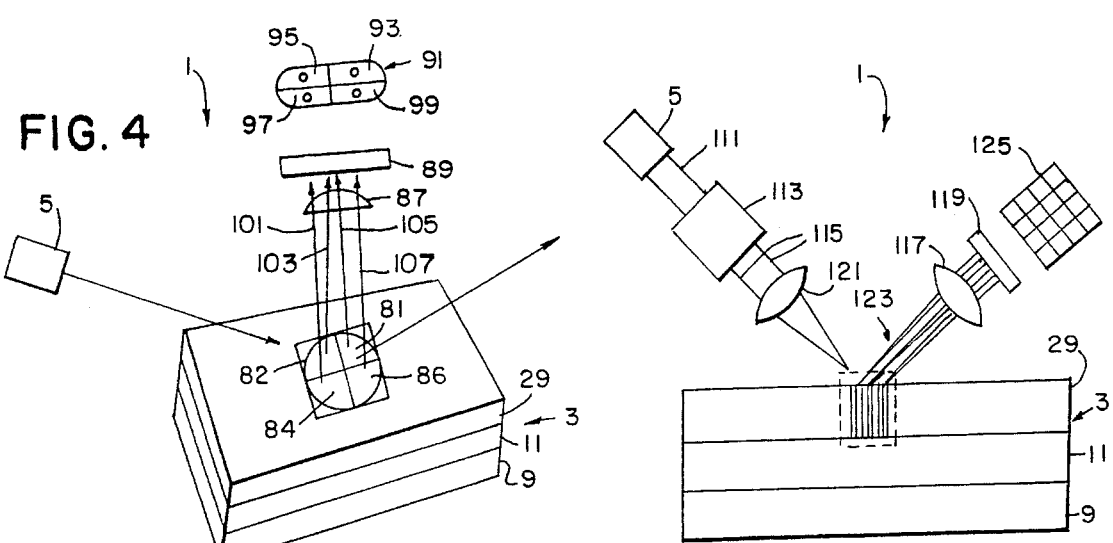
FIG. 4
FIG. 5
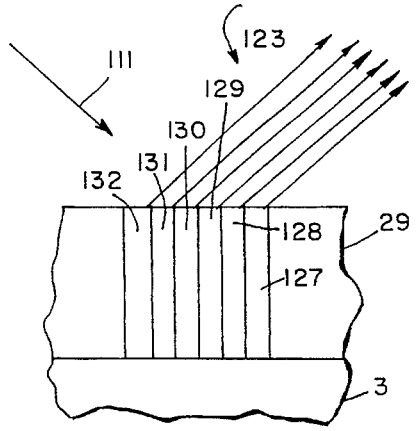
FIG. 6
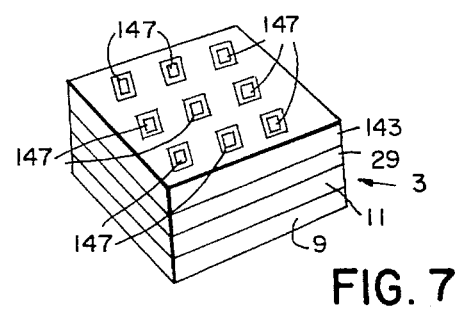
FIG. 7
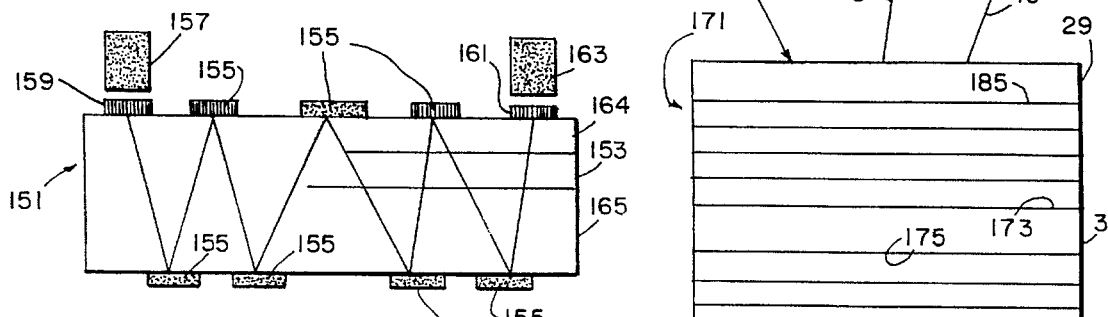
FIG. 8
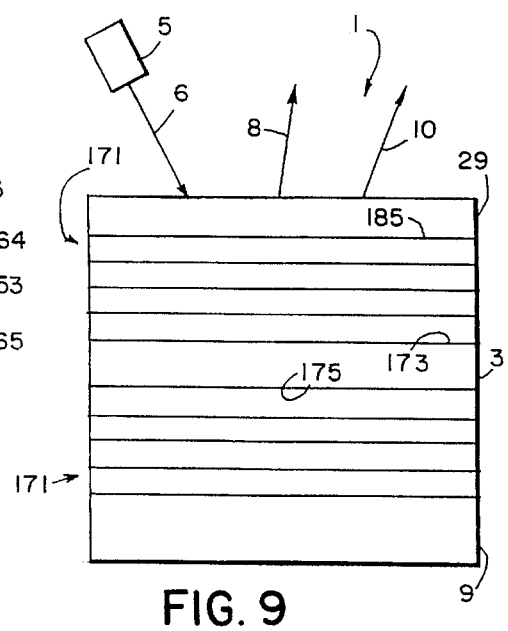
FIG. 9

OPTICAL CHEMICAL SENSOR AND METHOD USING SAME EMPLOYING A MULTIPLICITY OF FLUOROPHORES CONTAINED IN THE FREE VOLUME OF A POLYMERIC OPTICAL WAVEGUIDE OR IN PORES OF A CERAMIC WAVEGUIDE

BACKGROUND OF THE INVENTION

This invention relates to fluorescent sensors for chemical analysis.

Optical sensors are used in the determination of the chemical properties of liquid or gas-phase analytes. Existing sensors typically place the sensor material either in the evanescent field of the waveguide or at the tip of an optical fiber. The sensitivity of sensors based on evanescent field excitation is limited by the quantity of fluorescence coupled to the waveguide or fiber structure. The total quantity of fluorescence collected at a photodetector is also limited by inefficiencies associated with coupling light from the source to the optical waveguide or optical fiber. The specificity of fluorescent chemical sensors is limited by interferences associated with chemical reactions between the sensor material and materials other than the analyte.

Needs exist for optical waveguide sensors that can increase specificity, sensitivity and precision of fluorescent chemical sensors.

SUMMARY OF THE INVENTION

The present invention relates to optical sensors for identifying and measuring concentrations of chemical analytes in either gaseous or liquid phase. The invention provides optical instruments for chemical and biochemical analysis of materials, gases and liquids. The instruments are used for chemical detection of toxic or hazardous materials, in environmental monitoring, and for evaluating process conditions in chemical processing, food processing, or pharmaceutical manufacturing operations. Other applications are in pollution exhaust monitoring in the energy conversion industry, solvent monitoring in distillation processes, and in biomedical analyses.

A sensor according to the invention is used in measuring concentrations of gaseous pollutants, toxic chemicals or materials important in chemical process operations located in the vicinity of the sensor. The present invention relies for its operation on changes in fluorescence emitted from fluorophores either incorporated in optical waveguides or deposited on optical waveguides resulting from exposure of the fluorophores to analytes of interest.

The specificity of optical chemical sensors is limited because of the wide range of chemical reactions between sensor materials and materials other than the analyte of interest. The present invention addresses that problem through the formation of a vector quantity based on the response of several fluorescent sensors, each sensor having a different sensor material or host material. The total response, given in terms of a chemometric measure of each of the fluorophore responses, is specific for a particular analyte and allows for calibration of the instrument during operation. In situ calibration during sensor operation in turn improves the accuracy of the instrument in each measurement.

The present invention uses a light source, which may be a laser, a light-emitting diode or any other modulatable lamp or illumination device, to excite fluorescence in a sensor material incorporated either in an optical waveguide structure or in a coating on a waveguide structure. The key to the achievement of the present invention is that the optical waveguide can be prepared from porous polymeric or ceramic materials, thereby allowing diffusion of the analyte to a fluorophore contained within the waveguide. In one embodiment, light propagates at an angle to the waveguide. Light measuring components such as a series of light-sensitive photodiodes or a single charge-coupled device camera are used to receive the signal from the waveguide sensor. The light-induced fluorescence is modified by the optical waveguide. The waveguide reflects part of the incoming light at the angle of incidence. Part of the light entering the waveguide excites fluorescence of the fluorophore trapped within the waveguide or deposited on the waveguide. Some fluorescence is trapped in a guided optical mode within the waveguide, and some fluorescent light is reradiated from the waveguide structure. A photodetector is positioned near the waveguide to allow only a restricted field of view of light coming from the waveguide or from the material deposited on the waveguide. Light detected from the waveguide structure contains information concerning the state of the fluorophore which, in turn, contains information about the presence of the analyte.

Multiple analytes may be placed in the optical waveguide or above the optical waveguide through a wide range of techniques. Examples of methods used to produce optical waveguide structures, such that multiple waveguide structures (each containing a different fluorophore) can be deposited on a single sensor element, include but are not limited to the following approaches.

Free standing polymer materials and glass materials can be overlaid with a polymer or ceramic material of refractive index such that an optical waveguide is formed. As an example, polyimide can be deposited on soda-lime glass by following the procedure outlined below. The polyimide films are prepared by spin-coating a solution of polyimide in butyrolactone (Probimide 414, OCG Microelectronic Materials, Inc.) along with an adhesion promoter onto clean glass slides to form a waveguide that is approximately five microns thick. The waveguide structure is baked at approximately 240 degrees Centigrade under a nitrogen atmosphere. The polyimide to exposed to ultraviolet light at 365 nm. A fluorophore is then entrained in the polymer by dye diffusion. Next, the polyimide/dye probe is exposed to ultraviolet light at 365 nm wavelength and approximately 0.75 Joule per square centimeter light energy.

Optical waveguides can also be prepared by laser ablation of aluminum in an oxidizing environment to provide a porous ceramic waveguide structure. Fluorophores are deposited onto the waveguide structure by solution-based procedures. For example, a fluorophore-containing waveguide, such as nile blue A perchlorate in polyimide (Probimide 414, OCG Microelectronic Materials, Inc.), can be coated with oxazine 720 or oxazine 750 in nafion. Nafion perfluorinated ion-exchange powder is available as a 5% solution in Methanol (Aldrich 27,470–4) and can be used directly as received from Aldrich after adding an appropriate quantity of methanol to reach the desired polymer concentration. A 0.3% nafion solution in methanol together with oxazine 720 is optimal for sensing dimethyl methyl phosphonate (DMMP). Layers of oxazine 720/nafion or oxazine 750/nafion can be formed by placing 1.5–2.0 ml of solution on a previously prepared polyimide film. By following that procedure, a fluorophore can be deposited over a waveguide structure, which waveguide structure itself contains another fluorophore. Patterns of fluorophores are produced by dicing the optical waveguide structures fabricated with a range of polymer/dye combinations as the outer coating and adhering those sensor components in a predetermined pattern for sensor operation. The dye/polymer coatings can also be prepared by adhering a wire mesh, a laser-cut array of cells, or any other means of partitioning the surface coating to the waveguide structure, and then filling in the cells using an ink-jet printer, a capillary feed array or other fluid moving apparatus. The array of fluorophores can also be produced by microlithographically producing cells in the waveguide structure or in a layer adhered to the waveguide structure. The optical waveguides and the coatings can be prepared through sol-gel methods of deposition, solvent methods of polymer deposition, and methods involving ablation of a material forming a waveguide structure. In addition, the waveguide can be produced from a combination of deposited sol-gel and polymer sources.

The patterned waveguide structure is then illuminated either by a steady light source providing multiple spots of illumination or by moving the waveguide with respect to the optical source to illuminate one section of the patterned waveguide at a time. In one configuration of the proposed sensor, a fanout grating is used to produce multiple spots after illumination by a laser beam. In a second configuration, a holographic optical element is used to produce multiple spots.

Remote operation of the present invention can be achieved by using optical fibers. The signal from the optical source is guided to the optical waveguide by an optical fiber, and the fluorescent signal from the waveguide structure is detected using one or more optical fibers.

A preferred embodiment of the present invention includes electronically or piezoelectrically modulating the position of the excitation source beam on the optical waveguide array. Electronic modulation of beam position is accomplished using an electroptic material such as lithium niobate or a ferroelectric liquid crystal that exhibits a change in refractive index because of an applied voltage to steer the excitation beam from one fluorophore to another on the optical waveguide surface. In that manner, changes in fluorescence from multiple fluorophores or fluorophores embedded in differing responsive materials are monitored and summed to provide a total instrument response. A synchronous detector can be used to determine differences in phase and amplitude of fluorescence originating from different sensors on the waveguide structure. Along with various synchronous detection circuits, other techniques known in the area of modulation spectroscopy can be used to extract signals from noise.

The optical chemical sensor of the invention uses a multiplicity of fluorescence data to provide information on the identity and concentration of a chemical analyte in the presence of interferents. The preferred optical chemical sensor is based upon an optical waveguide produced by deposition of multiple layers of solvent-deposited polymers, each containing fluorophores, or by multiple layers of sol-gel deposited ceramic layers, each layer containing more or less fluorophore sensor material, or other optical waveguide structures that are excited by a light source at an angle to the waveguide surface. Fluorescence is detected either at a fixed angle to the waveguide surface or through a plurality of angles with respect to the waveguide surface. It is noted that the fluorophores contained in the optical waveguide constitute a resonator structure such that the fluorescence from within the cavity formed by the optical waveguide is enhanced with respect to a fluorophore outside the cavity. Similarly, the effect of the optical waveguide on a fluorophore deposited within the evanescent field of the waveguide is seen as an enhancement of interaction between the cavity and waveguide structures.

Excitation of fluorescence in the presence of the optical waveguide structure provides an enhancement of the optical signal derived from the sensor and allows the sensor to operate without direct coupling to each of the waveguide structures exciting the range of fluorophores necessary for analyte detection. When oxazine 720 in nafion is deposited on a glass optical waveguide structure having a polyimide film, the fluorescence signal is increased by almost a factor of ten over the signal measured when oxazine 720 is deposited over glass alone. It is noted that this sensor responds significantly to the presence of water vapor. Use of oxazine 750 instead of oxazine 720 provides a sensor with much less response in the presence of water vapor. Thus, a sensor containing oxazine 720 and oxazine 750 allows for a measure of water vapor concentration.

One preferred optical chemical sensor contains a multiplicity of receptors positioned as to form an array. An optical sensor according to the invention detects changes in fluorescence amplitude, frequency, decay time, polarization, saturation intensity and stability with temperature. A pump-probe approach may also be used to provide additional data from each element of the fluorophore array.

In a preferred optical chemical sensor, the light illuminating the optical waveguide is generated by a semiconductor laser diode. In the oxazine 720/nafion/polyimide system, the fluorescence excited by a laser emitting at 633 nm–650 nm can be used to detect the presence of DMMP, ammonia or water. Light entering the sensor structure is reflected from the optical waveguide, from partial mirrors deposited at the sensor surface, or from disturbed Bragg reflectors produced in the body of the waveguide or at the edges of the waveguide. The light passes through the fluorophore contained within the body of the sensor structure or interacts with a fluorophore deposited at the surface of the sensor structure. The output optical signal from that sensor body is adapted for use with optical fiber transmission.

The invention provides an optical sensor for identifying and measuring concentrations of chemical analytes in gaseous or liquid phase. The sensor relies on the change in fluorescence emitted from fluorophores incorporated in an optical waveguide or on top of an optical waveguide after exposure to the analyte of interest. The optical waveguide is produced by deposition of multiple layers of polymeric or ceramic materials, such that the refractive indexes of a guiding layer and cladding regions are controllable. By selecting polymeric and ceramic materials with sufficient porosity or diffusional characteristics and by allowing the entire structure to be diffusionally thin to the analyte of interest, changes within an optical cavity produced by interaction with fluorophoric sensor materials can be monitored. Since the waveguide structure is itself seen as an optical cavity, accessibility without direct optical coupling to each sensor component allows rapid evaluation of a wide range of analytes through chemometric methods of analysis. The change in fluorescence from each fluorophore incorporated within or on the optical waveguide is summed as a vector response and evaluated using digital signal processing techniques. This invention is useful in measuring the concentration of gaseous pollutants, toxic chemicals or process products present about the sensor.

The present invention is an improvement over existing sensor instruments. The fluorophore is contained in the porous optical waveguide, in an optical resonator structure, on top of a porous optical waveguide, or on top of an optical resonator structure. That improvement enhances the fluorescence effect. Additionally, the improvements, coupled with the positioning of a multiplicity of receptors in or on the patterned waveguide or patterned optical cavity, eliminates the need for prism, grating or end-fire coupling to the waveguide or cavity and allows modulation of the excitation beam position to gather precise data on differences in fluorescence of an array of fluorophores in the presence of an analyte. Also, by using and summing a multiplicity of fluorescent data, the present invention has greater specificity, decreased noise effects and higher accuracy.

These and further and other objects and features of the invention are apparent in the disclosure, which includes the above and ongoing written specification, with the claims and the drawings.

BRIEF DESCRIPTION OF THE DRAWINGS

FIG. 4 schematically shows a coated optical waveguide having a plurality of regions with fluorophores and hosts and an optical array detector to monitor the fluorescence from each section of the coating.

FIG. 5 schematically shows an array of fluorophore/host regions contained in a coating over an optical waveguide configured as an optical cavity. Fluorescence is detected by a photodetector array.

FIG. 6 is an enlarged schematic detail from FIG. 5.

FIG. 7 schematically shows selectively depositing a range of fluorophores and hosts on an optical waveguide structure.

FIG. 8 shows an alternate embodiment of chemical sensing using optical fibers to deliver light and carry away the signal.

FIG. 9 shows an optical waveguide that uses an optical cavity having dielectric mirrors to increase cavity resonance quality.

DETAILED DESCRIPTION OF THE DRAWINGS

Figures 1, 2, 3:
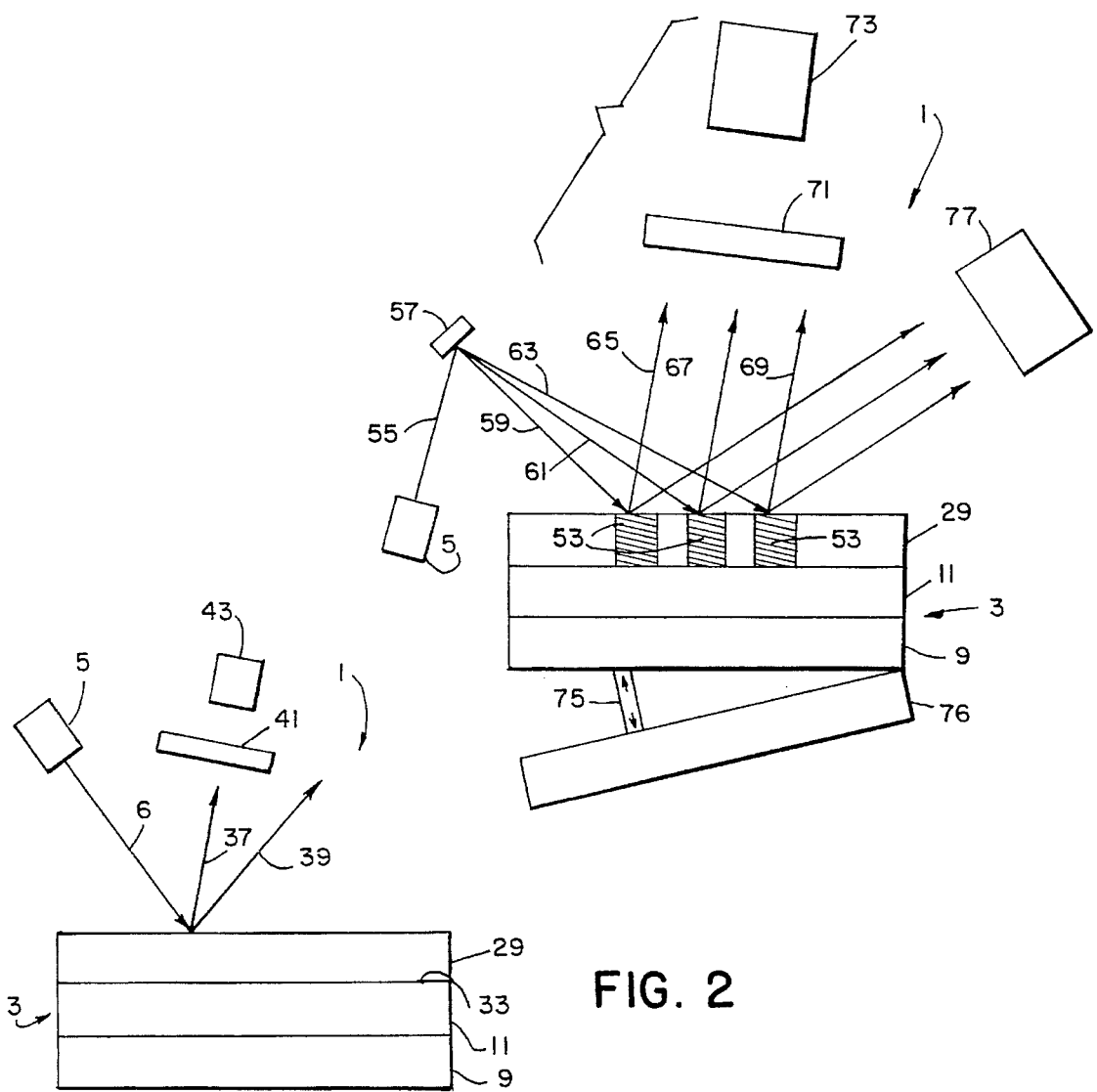
FIG. 1 is a schematic illustration of a fluorescent waveguide optical sensor in which the waveguide forms an optical cavity and light excitation is at an angle to the waveguide.
FIG. 2 is a schematic illustration of a fluorescent waveguide optical sensor having a fluorophore-containing coating layer applied to the upper surface of the waveguide.
FIG. 3 schematically shows the use of a moving mirror to modulate the position of an excitation beam over a structure produced by depositing a chemically sensitive coating over an optical waveguide containing fluorophores.

Referring to the drawings and initially to FIG. 1, an optical sensor 1 identifies and measures concentrations of chemical analytes in gaseous or liquid phases. The optical sensor 1 includes an optical waveguide 3, a light source 5 and a detector 7. FIG. 1 shows one embodiment of the present invention. The optical waveguide 3 has a substrate layer 9 and an overlying layer 11. Possible materials for the substrate layer 9 include polymer and glass. The overlying layer 11 is a polymer or ceramic material having a refractive index such that an optical waveguide is formed. The overlying layer 11 contains fluorophores 13. In one embodiment the overlying layer 11 is porous, thereby forming a porous optical waveguide 3. One possible porous overlying layer 11 is a polyimide layer. When a porous optical waveguide 3 is created, fluorophores 13 are deposited in the overlying layer 11. Multiple fluorophore regions can be incorporated.

As shown in FIG. 1, a light source 5 illuminates with wave energy 6 the porous optical waveguide 3 containing the fluorophores 13 at an angle. Fluorescence is generated within the waveguide 3. The fluorescence is dependent on the interaction of the fluorophores 13 in the overlying layer 11 of the waveguide 3 with a chemical analyte. A detector 7 positioned near the waveguide 3 detects the fluorescence 8 from the optical waveguide 3. Reflected light 10 from the source 5 is not detected.

FIG. 2 shows another embodiment of the present invention having an optical waveguide 3 with an overlying layer 11 that contains fluorophores. A thin coating 29 containing fluorophores is applied to the upper surface 33 of the layer 11 of the optical waveguide 3. Light 6 emitted from a light source 5 illuminates the optical waveguide 3, thereby exciting the fluorophores contained in the overlying layer 11 of the waveguide 3. Light emitted from those fluorophores causes the fluorescent materials in the coating layer 29 to fluoresce. The fluorescence from the material in the coating layer 29 is dependent on the interaction of the fluorophores in the coating layer 29 with a chemical analyte. A detector 43 positioned near the waveguide 3 detects the fluorescent signal 37. Light detected from the waveguide contains information concerning the states of the fluorophores which, in turn, contain information about the presence of the analyte.

As shown in FIG. 2, fluorescence emitted from the optical waveguide 3 interacts with fluorophores or absorbers present in the coating layer 29 and exhibits an angular dependence in emission intensity. Some incoming light is reflected 39 at the angle of incidence and is not detected. Some light is re-emitted and is blocked by an optical filter 41 designed to separate light at the excitation wavelength from light 37 emitted as fluorescence. An angle-resolvable photodetector 43 is used to determine fluorescence amplitude.

FIGS. 1 and 2 show methods of excitation and detection of the present invention. Light 6 from a light source 5, which may be a semiconductor diode laser, a light-emitting diode, or an optical lamp, impinges upon an optical waveguide 3, thereby exciting a fluorescent material or mix of fluorescent material contained within the waveguide or in the evanescent field of the waveguide. Where the waveguide forms an optical cavity, the fluorescence is preferentially emitted in a given direction and may be amplified or quenched depending upon the available modes of the waveguide. Inserting a polarizer between the fluorescence signal, the optical filter and the photodetector allows the instrument to monitor changes in fluorescence resulting from waveguide response to a chemical analyte.

Patterns of fluorophores can be produced in the waveguide or in the thin coating layer covering the upper surface of the waveguide. The patterned waveguide structure is illuminated through the use of a steady light source providing multiple spots of illumination, through movement of the waveguide with respect to the optical source to illuminate one section of the patterned waveguide at a time, or through other methods of lights modulation.

FIG. 3 shows a horizontal optical waveguide 3 coated with several regions 53 of differing fluorophores in differing host materials. In one embodiment, the position of the beam 55 is modulated by a movable mirror 57. The mirror 57 directs the beam 55 from position 59 to position 61 or position 63. Fluorescent signals, depicted by 65, 67 and 69, are generated and detected through optical filter 71 by photodetector 73. A piezoelectric mover 75 fixed on a base 76 alters the angle of fluorescence detection for each position of the pump beam. Photodetector 77 monitors the reflectance of the surfaces at position 59, position 61 and position 63 and provides an indication of changes in absorbance with time. Fluorescence and reflectance/absorbance data can be advantageously used in analyte detection. In one embodiment, signals 63, 67 and 69 at angles away from the specular reflection maximum are detected by a pair of photodetectors such that one half of the signal passes an optical filter 71 to remove light at the excitation wavelength and the other half of the signal removes light at any wavelength other than the excitation wavelength. That allows for the simultaneous detection of fluorescence and scattered light from the instrument surface. Additional information on fluorescence characteristics is provided by modulating the angle of the waveguide 3 to the incident beam, by modulating the angle of acceptance of the photodiode 77, or by using an array detector to quantify the maximum angle of fluorescence.

FIG. 4 shows one embodiment of the present invention wherein a multiplicity of fluorophore/host regions 81, 82, 84, 86 are excited by an excitation light source 5, such as a stationary pump beam. The fluorescent signals 85 are collected and imaged by a lens 87, are passed through an optical filter 89, and are directed onto a group of photodetectors 91. The use of individual photodetectors 93, 95, 97, 99 provides for evaluation of the fluorescence decay of fluorescent signals 101, 103, 105, 107 from each region 81, 82, 84, 86. To evaluate the fluorescence decay, the excitation light source 83 is modulated from 20 Khz to 100 MHz. The phase delay through each fluorophore/host is related to the relative fluorescence decay of each fluorophore/host. The decay is measured using phase-sensitive detectors operating on the electronic signals produced by each photodiode.

FIG. 5 expands on the embodiment of the present invention shown in FIG. 4. An excitation beam 111 is converted to a multiplicity of beams using a beam converter 113, such as a fanout grating, an holographic optical element, a series of beamsplitters, or a series of beamsplitting optical couplers. Multiple beams 115 are focused onto the coating layer 29 of the optical waveguide 3 by a lens 121. The resulting fluorescent signals 123 are focused through a lens 117 and a filter 119 on a detector 125, such as a plurality of photodetectors, a photodetector array, or a camera. Detector 125 can be an intensified diode array or an intensified charge coupled device camera. The excitation beam is modulated at a frequency from 20 KHz to 100 MHz. The image intensifier is modulated at the same frequency or at a range of offset frequencies to allow for detection of regions of varying fluorescence decay across the waveguide structure.

FIG. 6 shows a detail of FIG. 5. Multiple sections 127, 128, 129, 130, 131, 132 are positioned in the coating layer 29 covering the upper surface of the optical waveguide 3. Each section contains a different fluorophore/host combination. When excited by beams 111 from the light source, fluorescence signals 123 are emitted separately from each section 127, 128, 129, 130, 131. The signals 123 are monitored and differentiated to provide distinct responses or summed to provide an overall response.

In preferred embodiments of the present invention, patterns of fluorophores are produced in the waveguide or in the coating layer. FIG. 7 shows one embodiment wherein a patterned coating layer 29 is prepared using a laser-cut form 143 adhered to the waveguide structure 3. The form 143 permits the deposition of multiple fluorophore/host regions 147 in the cells cut from the form 143. When the form 143 is brazed onto the coating layer 29 of the waveguide 3, the regions 147 are filled using an hydraulic array, an ink jet printer, or other methods of sol-gel transport.

FIG. 8 shows another embodiment of the present invention The sensor body 151 is comprised of an optical waveguide 153 acting as an optical cavity. The waveguide 153 located on substrate 165 is either coated with a fluorophore/host combination 164 or surrounded by dielectric or metallic partial mirrors prior to coating. External mirrors 155 are be used to direct the light through the waveguide 153. Light enters the waveguide 3 through an optical fiber 157 that is optically coupled to the waveguide 153 by an input coupling port 159. Light coupled into the waveguide 153 is reflected multiple times. The fluorescence signal leaves the waveguide 153 at output port 161 through an optical fiber 163. The mirrors control the reflection of the light input and the fluorescence signal output thereby allowing the fluorescence signal to be separated from reflected or scattered light. That occurs as a result of the angular dependence of fluorescence within the structure. The light energizations and the fluorescence signal detections may be modulated or filtered to insure against erroneous detection of the input as an output signal.

FIG. 9 shows an embodiment of the present invention having multiple layers 171 deposited on the top surface 173 and the bottom surface 175 of the waveguide 3. Each layer 171 is a pair of dielectrics. In one embodiment, the sensor is produced by deposition of multiple layers 171 of solvent-deposited polymers, each containing fluorophores. In a second embodiment, the sensor is produced by deposition of multiple layers of sol-gel ceramics, each layer containing more or less fluorophore sensor material. A substrate 9 is positioned below the bottom surface 181 of the bottom layer and a coating layer 29 is positioned above the top surface 185 of the top layer. The dielectric layers function as dielectric mirrors and provide for vertical resonance. The sensor is designed to transmit the incident beam and reflect the fluorescence.

While the invention has been described with reference to specific embodiments, modifications and variations of the invention may be constructed without departing from the scope of the invention, which is defined in the following claims.

We claim:

1. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the optical waveguide further comprises a substrate layer and a porous overlying layer, the porous overlying layer containing the fluorophores, and wherein the substrate layer has a lower refractive index than the overlying layer.

2. The apparatus of claim 1, wherein the substrate layer is glass and the overlying layer is a polymer material.

3. The apparatus of claim 1, wherein the substrate layer is a polymer material and the overlying layer is a polymer material.

4. The apparatus of claim 1, wherein the light source is modulatable and wherein the light source is directed toward the waveguide at an angle for exciting the fluorophores.

5. The apparatus of claim 1, wherein the light source is a modulated light source directed toward the waveguide for producing a modulated light signal that excites the fluorophores in the optical waveguide and generates the fluorescence signals.

6. The apparatus of claim 5, further comprising an electronic light modulator connected to the light source for modulating the light source and a signal processor connected to the light modulator and to the detector for sequentially modulating the light source and collecting an electronic signal from the detector for providing improved signal-to-noise ratio, for determining lifetimes of the fluorescence signal, for conditioning electronic signals and for identifying and measuring concentration of an analyte.

7. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the detector comprises an array of photodetectors.

8. The apparatus of claim 7, wherein the array of photodetectors comprises an intensified charge coupled device camera.

9. The apparatus of claim 1, further comprising an optical filter positioned between the optical waveguide and the detector for filtering the fluorescence signal.

10. The apparatus of claim 9, further comprising a lens positioned between the filter and the optical waveguide for focusing the fluorescence signal.

11. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the waveguide has at least two regions of differing fluorophores in different host materials.

12. The apparatus of claim 11, wherein the detector further comprises multiple photodetectors equal in number to a number of the regions, and wherein each photodetector receives and evaluates a fluorescence signal from only one region.

13. The apparatus of claim 12, further comprising a lens positioned between the photodetectors and the waveguide for focusing the fluorescence signals and an optical filter positioned between the photodetectors and the lens for filtering the fluorescence signals.

14. The apparatus of claim 12, further comprising an optical filter positioned between the photodetectors and the waveguide for filtering the fluorescence signal.

15. The apparatus of claim 14, further comprising a movable mirror intermediate the light source and the waveguide for modulating light from a light source and directing the light on different regions of the waveguide.

16. The apparatus of claim 14, further comprising a piezoelectric mover connected to the waveguide for modulating the position of the waveguide with respect to light beams from the light source.

17. The apparatus of claim 12, further comprising a beam converter positioned between the light source and the waveguide for converting a single collimated beam to multiple beams.

18. The apparatus of claim 17, wherein the beam converter is selected from the group consisting of a fanout grating, an holographic optical element, a series of beamsplitters, and a series of beamsplitting optical couplers.

19. The apparatus of claim 17, further comprising a lens positioned between the beam converter and the waveguide for focusing the multiple beams from the converter on different regions of the waveguide.

20. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the detector comprises at least two photodetectors, and wherein a first photodetector is positioned near the waveguide for detecting reflected light, and a second photodetector is positioned above the waveguide for detecting fluorescence signals.

21. The apparatus of claim 20, further comprising an optical filter positioned between the second detector and the waveguide for filtering the fluorescence signals.

22. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the optical waveguide further comprises a substrate layer and an impervious overlying layer, the impervious overlying layer containing fluorophores, and wherein the substrate layer has a lower refractive index than the overlying layer, and further comprising a coating layer positioned over the impervious layer of the waveguide, the coating layer containing fluorophores that fluoresce upon excitation from signals emitted from fluorophores in the impervious layer that interact with a chemical analyte.

23. A chemical sensor apparatus comprising an optical waveguide, fluorophores positioned in the waveguide, a light source for exciting the fluorophores and generating fluorescence signals, and a detector positioned near the waveguide for sensing the fluorescence signals, further comprising an input port on the waveguide, an output port on the waveguide, a first optical fiber optically coupled to the waveguide at the input port for delivering light signals to the waveguide, and a second optical fiber optically coupled to the waveguide at the output port for collecting the fluorescence signals.

24. The apparatus of claim 23, further comprising multiple dielectric mirrors attached to the waveguide for directing light through the waveguide for providing reflection back into the waveguide, and wherein the mirrors are coated with fluorophores.

25. The apparatus of claim 23, wherein the first optical fiber is optically coupled to the input port by a grating.

26. The apparatus of claim 23, wherein the waveguide has a free space interconnect and the light signal enters the interconnect through a lens or a lens array.

27. The apparatus of claim 23, wherein the output port is a grating.

28. The apparatus of claim 23, wherein the output port is a prism coupler.

29. A chemical sensor apparatus comprising an optical waveguide, fluorophores positioned in the waveguide, a light source for exciting the fluorophores and generating fluorescence signals, and a detector positioned near the waveguide for sensing the fluorescence signals, wherein the waveguide has first and second opposite surfaces and further comprising dielectric layers deposited on the first surface and on the second surface of the waveguide, a coating layer positioned on a top dielectric layer, and a substrate positioned below a bottom dielectric layer, and wherein the dielectric layers serve as dielectric mirrors.

30. A method for identifying and measuring concentration of a chemical analyte in either gaseous or liquid phase comprising exciting fluorophores associated with an optical waveguide by using a modulated light source and creating fluorescence signals; trapping the fluorescence signals in the waveguide; transmitting the fluorescence signals from the optical waveguide; detecting the fluorescence signals; collecting the fluorescence signals; determining lifetime of the fluorescence signals; and converting the fluorescence signals to electronic signals, further comprising propagating the fluorescence signals from the waveguide through an internal grating structure, further comprising propagating a collimated beam from the light source, converting the beam to multiple beams, and directing the multiple beams on multiple fluorophore/host regions in the optical waveguide.

\* \* \* \* \*